United States Patent
Ulrici et al.

(10) Patent No.: US 8,320,522 B2
(45) Date of Patent: Nov. 27, 2012

(54) METHOD FOR CREATING A TOMOGRAPHIC IMAGE

(75) Inventors: Johannes Ulrici, Darmstadt (DE); Erich Hell, Illingen (DE); Christian Beckhaus, Darmstadt (DE)

(73) Assignee: Sirona Dental Systems GmbH, Bensheim (DE)

( * ) Notice: Subject to any disclaimer, the term of this patent is extended or adjusted under 35 U.S.C. 154(b) by 129 days.

(21) Appl. No.: 12/855,085

(22) Filed: Aug. 12, 2010

(65) Prior Publication Data

US 2011/0033026 A1    Feb. 10, 2011

Related U.S. Application Data

(63) Continuation of application No. PCT/EP2009/051608, filed on Feb. 12, 2009.

(30) Foreign Application Priority Data

Feb. 12, 2008    (DE) .......................... 10 2008 008 733

(51) Int. Cl.
*A61B 6/14* (2006.01)
*A61B 6/00* (2006.01)

(52) U.S. Cl. .......................................... 378/38; 378/21

(58) Field of Classification Search ................. 378/4, 19, 378/38, 39, 62, 21, 51, 53; 382/128, 131, 382/132

See application file for complete search history.

(56) References Cited

U.S. PATENT DOCUMENTS

| | | | |
|---|---|---|---|
| 4,878,234 A | 10/1989 | Pfeiffer et al. | |
| 5,195,114 A | 3/1993 | Sairenji et al. | |
| 6,289,074 B1 * | 9/2001 | Arai et al. | 378/4 |
| 6,493,415 B1 | 12/2002 | Arai et al. | |
| 7,039,156 B2 * | 5/2006 | Arai et al. | 378/39 |
| 7,660,453 B2 * | 2/2010 | Lang | 382/132 |
| 7,676,022 B2 * | 3/2010 | Pantsar et al. | 378/39 |
| 2003/0235265 A1 | 12/2003 | Clinthorne et al. | |
| 2004/0066877 A1 | 4/2004 | Arai et al. | |
| 2005/0237324 A1 | 10/2005 | Guhring | |
| 2009/0168954 A1 | 7/2009 | Kia et al. | |

FOREIGN PATENT DOCUMENTS

| | | |
|---|---|---|
| DE | 41 33 066 A1 | 4/1992 |
| DE | 10 2005 055 896 A1 | 5/2007 |
| EP | 0 279 294 A1 | 8/1988 |

(Continued)

OTHER PUBLICATIONS

Sirilawan Tohnak et al., "Synthesizing panoramic radiographs by unwrapping dental CT data". Engineering in Medicine and Biology Society, 2006, EMBS 06, 28th annual international conference of the IEEE, IEEE, Piscataway, NJ, USA, Aug. 30, 2006, pp. 3329-3332, XP031390350. IBSN: 978-1-4244-0032-4, p. 3331; table 2.1.

Vergleich der Strahlenexposition bei der Digitalen-Volumen-Tomographie 'der Panoramaschichtaufnahme und der Computertomographie, Christoph Schnelle, Medizinische Fakultat der Heinrich-Heine-Universitat Dusseldorf, 2001, Seiten 1-5Seiten 1-5.

(Continued)

*Primary Examiner* — Irakli Kiknadze
(74) *Attorney, Agent, or Firm* — Fitzpatrick, Cella, Harper & Scinto (57) ABSTRACT

A method for creating a tomographic image in the manner of a dental X-ray panoramic tomographic image from a digital 3D volume exhibiting X-ray absorption values, comprising transradiating the 3D volume forming an object to be scanned virtually using a virtual X-ray source, recording the virtually produced image by a virtual detector, and moving the virtual source of X-rays and virtual detector virtually past the object to be scanned with formation of a sharp layer having a blurred area.

12 Claims, 5 Drawing Sheets

FOREIGN PATENT DOCUMENTS

| | | |
|---|---|---|
| JP | 2001-061834 A | 3/2001 |
| JP | 2003-175031 A | 6/2003 |
| WO | 2006-127416 A2 | 11/2006 |
| WO | 2007-054219 A1 | 5/2007 |

OTHER PUBLICATIONS

Das 3D-Rontgensystem Galileos, Ch. Scheifele und P.A. Reichart, ZWR-Das deutsche Zahnarzteblatt 2007, Seiten 615-617.

* cited by examiner

METHOD FOR CREATING A TOMOGRAPHIC IMAGE

CROSS REFERENCE TO RELATED APPLICATIONS

This application is a continuation of International Application No. PCT/EP2009/051608, filed Feb. 12, 2009 (published in German as International Publication No. 2009/101123 A1), and claims priority to German Patent Application No. 10 2008 008733.5, filed Feb. 12, 2008 and U.S. Provisional Patent Application No. 61/071,143, filed Apr. 15, 2008, each of which is incorporated by reference herein in its entirety, as if set forth fully herein.

TECHNICAL FIELD

The invention relates to a method for producing a tomographic image, in particular a panoramic tomographic image (PAN image), from a digital 3D volume which has X-ray absorption coefficients and which may have been produced, for example, from X-ray projection images by reconstruction methods. Such tomographic images are used for dental diagnostics.

The term "tomography" refers, in general, to the imaging of a two-dimensional layer of a three-dimensional object. Blurring tomography is a special kind of tomography in which a two-dimensional layer is produced without using 3D data. Blurring tomography is characterized by the fact that, when a film and an emitter are moved relatively to the object, points located in a so-called sharp layer of the object are always imaged at the same point of the film and are thus imaged sharply. However, points located outside the sharp layer are imaged on the film as blurred curves, which correspond to the mechanical movements of the emitter and the film in relation to the object.

The difference between blurring tomography and a 3D tomographic method is that the latter implements a projection from 3D onto 2D when computing a layer such that all object planes are represented with equal dominance normal to the projection axis without any one plane being distinguishable as a sharp layer by, say, superimposition.

PRIOR ART

EP 0 279 294 A1 discloses a dental X-ray diagnostics system for producing panoramic tomographic images of the jaw of a patient. The method described therein allows for representation of a layer in the object whose center is usually the jaw of the patient. For the purpose of producing a panoramic tomographic image, an emitter-detector system is moved around an object to be imaged and the CCD detector lines are clocked out at a frequency that is modified in relation to the speed of movement in order to produce a tomographic image with blurring of the portions located outside the sharp layer.

Instead of generating an image in a predefined sharp layer, it is indeed possible to produce individual images by appropriately clocking out image information from the detector and to subsequently superimpose these individual images for a given layer position to form a panoramic tomographic image. Due to the comparatively small width of detectors normally used, always only portions of the object being imaged are detected and it is not possible to use these portions to create a 3D volume of the object being imaged. The use of such full frame sensors leads to the production of a large number of individual images. The number of individual images is equal to the number of line clocks occurring during the normal PAN rotation, which results in several thousands of individual images.

The use of commercially available dental X-ray systems operating according to the principle of digital cone beam volume tomography (DVT) involves joint movement of an emitter and a detector around the patient's head in a predefined x-y plane. The emitter and detector are moved in such a way that they rotate about a rotation axis located within the object to be imaged and extending in the z-direction. Projection images are produced from various positions of the emitter and detector along this circular path during rotation, which path describes an angle of at least 180°. A 3D volume is then computed from these projection images. This 3D volume contains information on location-dependent X-ray absorption coefficients or image data derived therefrom.

These values are implemented to form a panoramic image, which, however, is not a conventional panoramic tomographic image. In addition, the position and thickness of the layer to be displayed are adjusted or selected within the 3D volume and the X-ray absorption coefficients, which are summated from parallel transradiations executed normal to the layer, are processed and displayed as image data. This is disclosed, for example, in the dissertation "Vergleich der Strahlenexposition bei der Digitalen-Volumen-Tomographie der Panoramaschichtaufnahme and der Computertomographie" presented by Christoph Schnelle, Faculty of Medicine, Heinrich Heine University, Dusseldorf, 2001, pages 1 to 5 and in the article "Das 3D—Röntgensystem GALILEOS" by Ch. Scheifele and P. A. Reichart, ZWR—Das deutsche Zahnärzteblatt 2007, pages 615 to 617.

Although the result here is an X-ray image giving a visual impression, which is similar to a panoramic tomographic image produced using an orthopantomograph, structures located outside the sharp layer are not taken into account and there is no blurring effect.

Due to the longstanding diagnostic practice of users and the image data still contained in conventional PAN images in spite of blurring, it may be desirable, even if a radiographic 3D volume is available, to provide an X-ray image corresponding to a conventional panoramic tomographic image.

SUMMARY OF THE INVENTION

The fundamental idea of the invention relating to the provision of a tomographic image with X-ray systems capable of producing a 3D volume, is to compute the tomographic image from the previously produced 3D volume by simulating the blurring tomographic method of an orthopantomograph on a 3D volume and not by extracting a layer from the 3D volume.

In the method of the invention for the production of a tomographic image from a digital 3D volume which has X-ray absorption coefficients and which is particularly suitable for producing a dental X-ray panoramic tomographic image, the 3D volume is transradiated virtually using a virtual X-ray source and the resulting virtual image is recorded by a virtual detector. The virtual X-ray source and the virtual detector are moved virtually past the object being imaged and a sharp layer having a blurred area is formed.

The virtual sequence employed for imaging the 3D volume as an object and the collaboration of the virtual X-ray source and the virtual detector can be the same as used conventionally for producing a digital tomographic image having a blurred area.

Advantageously, structures, particularly anatomical structures such as the spinal column, which produce shadows in a tomographic image and are therefore undesirable, are removed from the computed 3D volume prior to producing the simulated tomographic image, for example by means of a search algorithm. The fact that the tomographic image is simulated following the removal of these structures leads to an improvement in the image quality, since the other structures still of interest to the observer are shown more clearly.

This applies both to the information directly concerning the teeth and to the additionally displayed information concerning the panoramic images hitherto computed from the 3D volume, as in a conventional PAN image.

In lieu, for example, of a fan beam, which emanates from a focus within the X-ray source, provision may be made for modifying the path taken by the rays by carrying out transradiation with a bundle of parallel rays to prevent distortion in the z-dimension, for example.

Advantageously, the course of the sharp layer of the computed tomographic image can be varied. In the case of conventional tomographic images, the location of the sharp layer for a given position in the object is not variable.

It is particularly advantageous if the distance of the sharp layer from the virtual focus or virtual detector can be varied normal to a focus-detector plane of rotation. This makes it possible to adapt the image to anatomical structures such as tilted teeth. While the standard imaging process is modified in this case, the remaining image information is retained.

In order to display other information, the thickness of the sharp layer shown may be varied, advantageously by changing the simulated detector width in combination with broadening of the fan beam and modification of the simulated speed of rotation of the X-ray source and detector.

The tomographic image may very advantageously be a panoramic tomographic image, and the virtual X-ray source and the virtual detector execute virtual movement around the 3D volume instead of around the patient's head. The distance of the virtual X-ray source and of the virtual detector from the sharp layer, the width of the virtual detector and the blurred portions can be the same as those used for creating a standard panoramic tomographic image. Also, attention can be paid to the beam angle at this point.

In addition, the various distances between the virtual X-ray source, the virtual detector and the respective center of rotation of the ray path can be modified. Since the commercially available devices for producing panoramic tomographic images differ from each other in terms of design, the panoramic tomographic images provided by the respective devices have device-specific features. It is possible to allow for such device-specific features, at least partly, when producing panoramic tomographic images from the 3D volume.

Furthermore, a single tooth X-ray image is also used as a tomographic image containing a blurred area, for example, in transversal tomographic images.

It is important that all modifications to the tomographic image can be effected purely on the basis of the existing projection images used for creating the 3D volume, without it being necessary to produce another X-ray image.

Furthermore, according to a development of the invention, a search algorithm can be used on the 3D volume before creating the virtual tomographic image, to automatically determine the location of a sharp layer in the object with reference to characteristic anatomical structures, for example by automatically determining the alveolar ridge and the teeth present therein. Once the location has been determined, the virtual imaging process can take place. Unlike in the case of real images, it can be ensured that individual anatomical peculiarities are always allowed for and do not lie outside a predefined, standardized sharp layer.

From a practical perspective, it is currently expedient to compute the 3D volume completely before carrying out simulation of the tomographic image. Alternatively, the production of the tomographic image can be simulated on the basis of the original projection images independently of the reconstruction of the 3D volume or as part of said reconstruction. The tomographic image including blurred areas will then be computed on the basis of the information obtained from the projection images.

Another aspect of the invention therefore relates to a method in which a blurred tomographic image is produced from projection images suitable for the purpose of producing a 3D volume by reconstruction methods. In this embodiment, it is not necessary to first compute a 3D volume having X-ray absorption coefficients from the projection images and then to evaluate the 3D volume by mathematical methods, but rather, to evaluate projection images themselves, for which purpose use may be made of some of the process steps known from the reconstruction methods, without having to compute a volume of the object to be imaged. This produces a tomographic image containing a sharp layer and blurred portions.

Here again, simulated PAN images or TSA images can be produced, which in terms of their image information come closer to conventional images than pure projection images.

BRIEF DESCRIPTION OF THE DRAWINGS

An exemplary embodiment of the invention is shown in the drawings, in which.

DESCRIPTION OF AN EMBODIMENT OF THE INVENTION

Figure 1A:
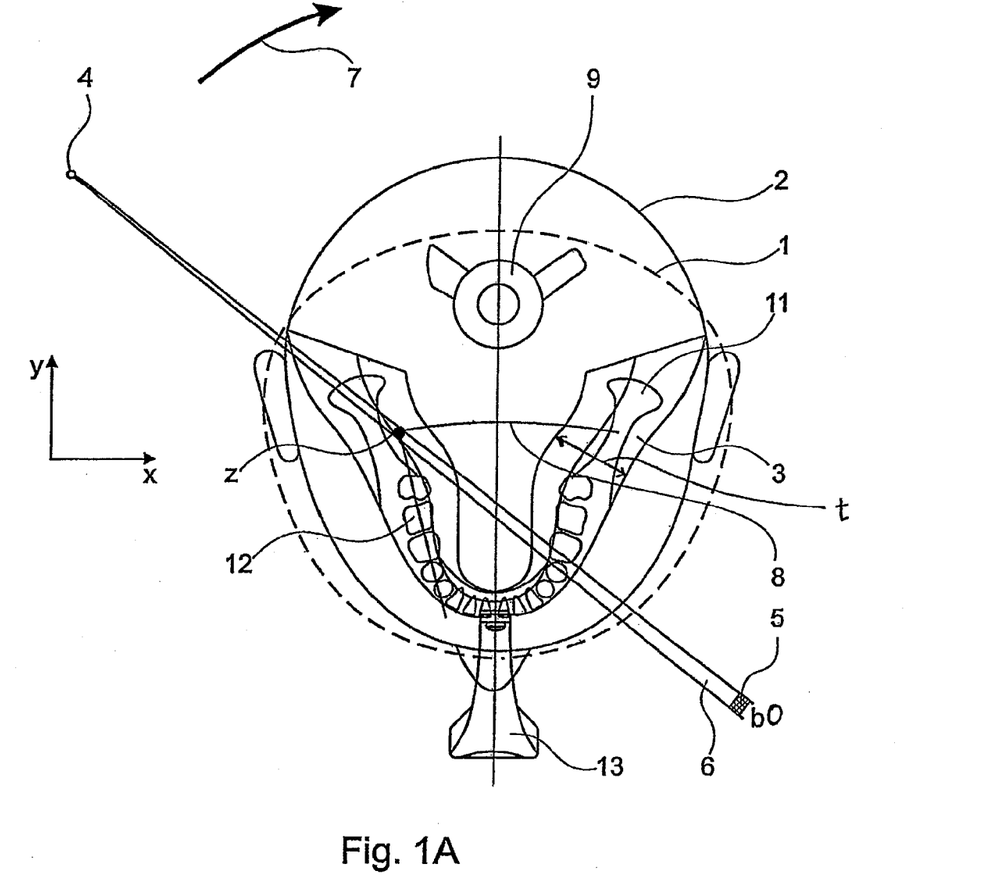
FIG. 1 is a diagram of the virtual imaging situation of a 3D volume for the production of a panoramic tomographic image having a sharp layer.

FIG. 1A shows a 3D volume 1 of a patient's head 2 as the object to be examined, which contains an image of a mandibular arch 11 and a plurality of teeth 12 in the form of information concerning X-ray absorption coefficients or image data derived therefrom. The 3D volume 1 can be the entire head 2 of the patient or only a part thereof, as shown, and the 3D volume 1 need not be entirely located within the patient's head 2. The tomographic method of the invention having a blurring effect is explained on the basis of this 3D volume 1, in which a sharp layer 3 extending through the 3D volume 1 of the patient's head 2 is simulated. The sharp layer 3 corresponds to a region of defined extent, a width t, and may be denoted by a line for the sake of simplicity.

The 3D volume 1 is, ideally, determined such that it contains all the anatomical features required for producing a panoramic tomographic image. Furthermore, the 3D volume 1 may also contain other anatomical regions, such as soft tissues like the nose and lips.

The 3D volume 1 shown in FIG. 1 and having X-ray absorption coefficients is transradiated virtually using a virtual X-ray source 4 located outside the 3D volume 1 in the present exemplary embodiment and having a virtual focus. Virtually attenuated rays of a virtual fan beam 6 are recorded via a virtual detector 5, which is likewise disposed outside the 3D volume 1 and has a width b0.

To effect imaging, for example, the X-ray absorption coefficients along the path of a ray of the virtual fan beam 6 having a defined cross-sectional area can be summated from the virtual X-ray source 4 to the virtual detector 5, the result then corresponding to the signal value of a pixel of a real detector. The non-linear absorption function for X-ray beams is also taken into account, if appropriate.

The virtual X-ray source 4 and the virtual detector 5 can also be disposed within the 3D volume 1. Although this does not enable a standard PAN image to be simulated in conventional manner, the image properties of this PAN simulation can be implemented in lieu of the panoramic image hitherto used.

A simulated panoramic tomographic image (FIG. 2) is produced by means of a simulated rotation 7 of the virtual X-ray source 4 and the virtual detector 5 at a simulated speed of rotation about a center of rotation Z within the object 1 to be imaged, the 3D volume 1, which rotation corresponds to the rotation carried out around the mandibular arch 11 when producing conventional PAN images. The center of rotation Z follows a curve 8 during the simulated rotation 7, as is known from conventional PAN images disclosed in the prior art. For the sake of clarity, a virtual bite element 13 is shown, which places the patient's head 2 in position when the patient bites thereon. The bite element 13 defines an occlusal plane located in this case in the x-y plane.

During simulated rotation 7, the virtual detector 5 is then clocked out virtually, i.e. the image data are generated in such a way that a sharp layer 3 having a thickness t and a blurring effect is produced outside the sharp layer 3, this corresponding to the triggering of real detectors.

When triggering a real CCD detector, the entire image registered on the detector is displaced by one line. If this triggering takes place in the direction opposed to the movement of the X-ray source/detector system, the object points located in the sharp layer 3 are always reproduced on the same point in the image, while the object points located outside the sharp layer move across the image and are thus blurred.

Unwanted structures 9 present in the 3D volume 1, for example the spinal column or the opposite mandibular arch, can be faded out before the simulated PAN image is produced.

Figure 1B:
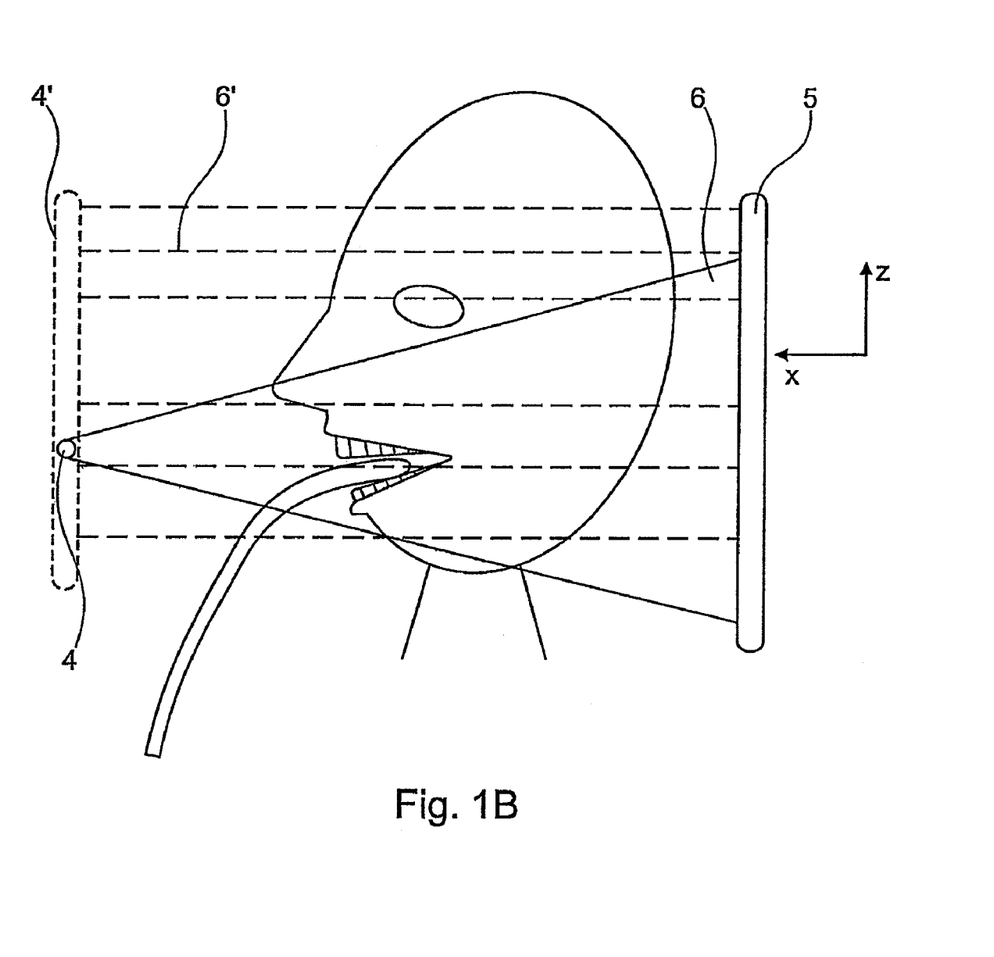

FIG. 1B is a diagrammatic section taken along the virtual fan beam 6 shown in FIG. 1A. It is apparent that the virtual fan beam 6 is also spread out in this x-z plane, emanating from the focus of the X-ray source 4 toward the virtual detector 5.

In lieu of the fan beam 6, a virtual transradiation can also be effected with a ray beam composed of parallel rays 6'. In that case, the focus of the X-ray source is conceivably of appropriately large dimensions and emits parallel rays. Unlike in the case of physical production of an image, such computed production of a panoramic tomographic image is readily possible.

Figure 2:
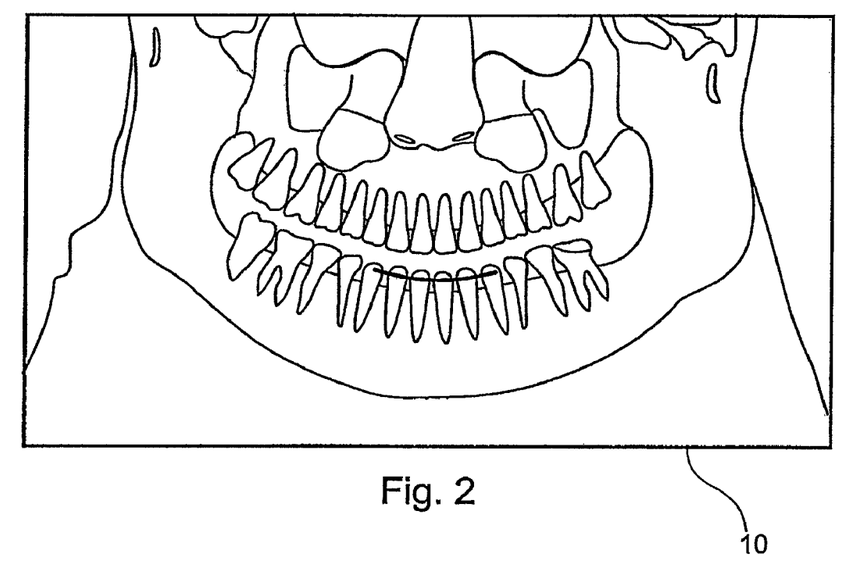
FIG. 2 is a tomographic image produced according to the principle shown in FIG. 1.

FIG. 2 shows a tomographic image 10 produced using the present method and it is obvious to the person skilled in the art that it approximates a conventional panoramic tomographic image in terms of its information content but with the spinal column removed.

Figure 3:
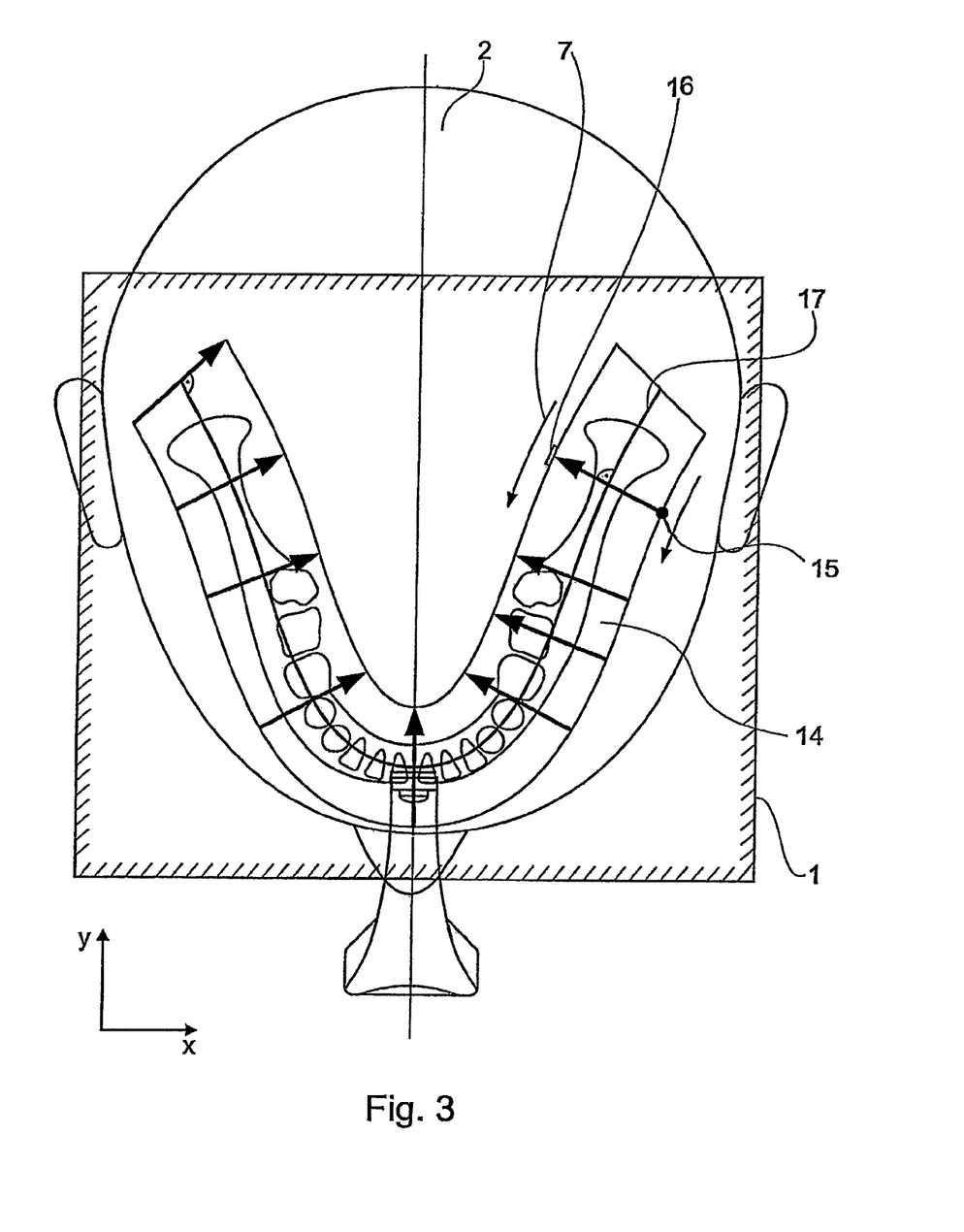
FIG. 3 is a diagram illustrating the production of a panoramic image according to the prior art.

FIG. 3 shows a diagram illustrating the production of a panoramic image according to the prior art. Based on a subregion 14, which is defined in the 3D volume 1 of the patient's head and which contains the sharp layer shown in FIG. 1, as regarded three-dimensionally, a virtual transradiation of only this subregion 14 is effected while the remaining 3D volume 1 is disregarded. A virtual X-ray source 15 and a virtual detector 16 are moved normal to the course of the subregion 14 along the latter in accordance with a path 17, and the resulting projections are displayed as an overall image 18 forming a panoramic image as shown in FIG. 4.

Figure 4:
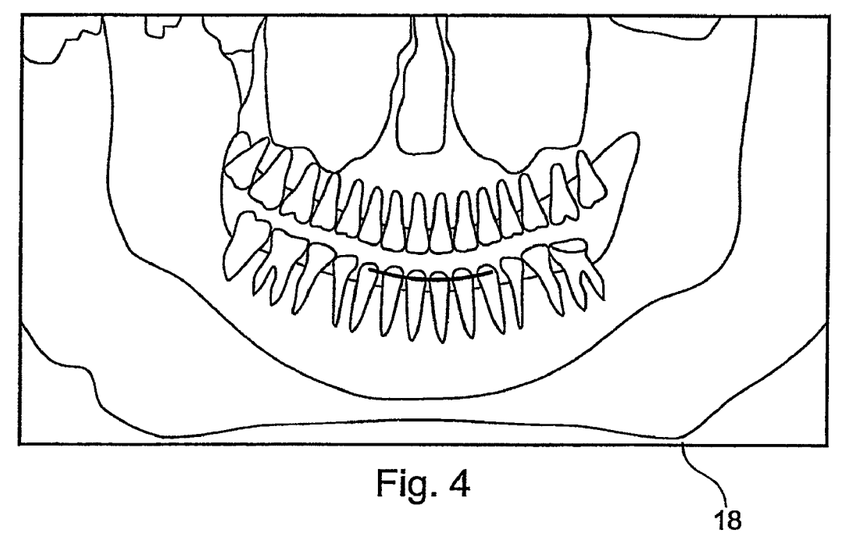
FIG. 4 is an image produced according to the prior art shown in FIG. 3, FIGS. 5A, 5B show a changed location of the sharp layer in the z-direction.

The image 18 shown in FIG. 4 is, to the person skilled in the art, not a tomographic image in the correct sense of the term, since the blurred areas of the image information outside the sharp layer are missing.

Figure 5A:
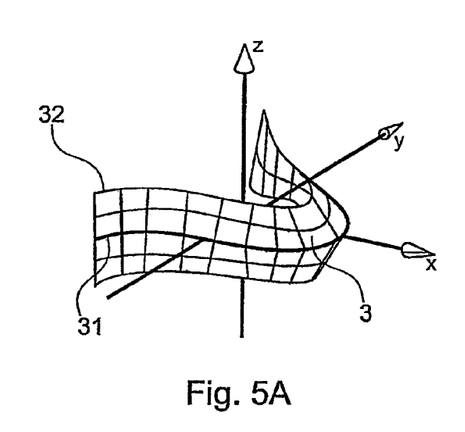

FIG. 5A shows, with reference to a midplane of the sharp layer 3, the manner in which the location of the sharp layer can be varied in the z-direction. The midplane of the sharp layer 3 follows the mandibular arch along a curve in the x-y directions and also varies in the z-direction in the example illustrated. This course is suitable when teeth 35, 36 of the patient are non-perpendicular to the x-y plane, as shown in detail in FIG. 5B.

The x-y plane coincides with the occlusal plane of the patient's head and line 31 corresponds to the midplane of the sharp layer in the occlusal plane. Line 32 corresponds to a midplane of the sharp layer above the occlusal plane and is thus displaced upwardly in the z-direction.

Figure 5B:
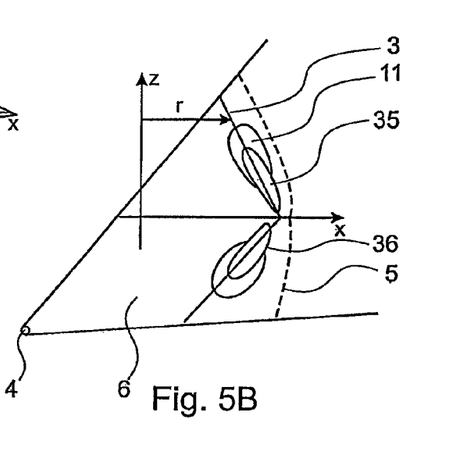

FIG. 5B shows the course of the sharp layer 3 in the region of the teeth 35, 36 located in a jaw arch 11 as a cross-section in the x-z plane. It is apparent that the midplane of the sharp layer 3 in the z-direction follows the course of the teeth 35, 36, i.e. the sharp layer 3 is curved with consequent variation of its distance from the z-axis in the z-direction.

During virtual transradiation, the virtual X-ray source 4 is disposed inside the teeth 35, 36 and the virtual fan beam 6 transradiates the jaw arch 11 outwardly from the inside. The virtual detector 5 is likewise curved. It can alternatively be straight and/or disposed at a greater distance from the midplane of the sharp layer 3.

Figure 6:
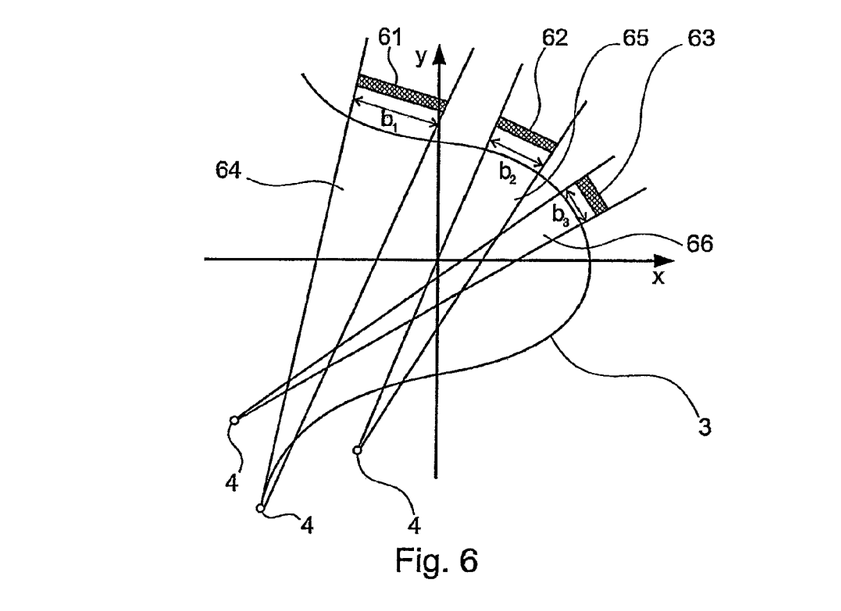
FIG. 6 shows an imaging situation implementing a narrow detector and a broad detector.

FIG. 6 is a diagram in which the detector width is variable thus making it possible to control the thickness of the sharp layer.

The figure shows three different virtual detectors 61, 62, 63 having a width b1 to b3 respectively and a virtual fan beam 64 to 66 of a virtual X-ray source 4, which is adjusted to correspond to the respective detector width. With such an arrangement, it is possible to change the thickness of the sharp layer 3, depicted here by a line, during simulated rotation. This effect is not possible in conventional X-ray systems for producing panoramic tomographic images. In conventional panoramic tomographic images, the width of the detector can vary according to manufacturer so that manufacturer-specific standard images can be provided by way of an adaptable detector width.

Furthermore, manufacturer-specific beam angles of the fan beam emanating from the X-ray source can be taken into account in order to simulate manufacturer-specific features.

In addition to panoramic tomographic images, it is also possible to produce transversal tomographic images (TSA image), in which, although the movement relative to the object is effected differently, a blurring effect occurs which produces a sharp layer.

The position of the sharp layer in the PAN image or in the TSA image can be customized or pre-selected for defined positions, for example, in order to provide a first adaptation to dimensional parameters. Furthermore, the position can also be defined automatically with reference to anatomical structures.

LIST OF REFERENCE SIGNS 1 digital 3D volume
2 patient's head
3 sharp layer
4 virtual X-ray source
5 virtual detector
6 virtual fan beam 7 simulated rotation of the virtual X-ray source 4 and the virtual detector 5
8 curve followed by the center of rotation Z during simulated rotation 7
9 unwanted structures
10 tomographic image
11 mandibular arch
12 teeth
13 bite element
14 subregion of the digital 3D volume 1
15 virtual X-ray source
16 virtual detector
17 path along which the virtual X-ray source 15 and the virtual detector 16 are moved
31 midplane of the sharp layer 3 in the occlusal plane
32 midplane of the sharp layer 3 above the occlusal plane
35 tooth
36 tooth
61 virtual detector
62 virtual detector
63 virtual detector
64 virtual fan beam corresponding to the width b1 of the virtual detector 61
65 virtual fan beam corresponding to the width b2 of the virtual detector 62
66 virtual fan beam corresponding to the width b3 of the virtual detector 63
b1 width of the virtual detector 5 or 61
b2 width of the virtual detector 62
b3 width of the virtual detector 63
r distance of the sharp layer from the z-axis
t thickness of the sharp layer 3
Z center of rotation of the simulated rotation 7

The invention claimed is:

1. A method for creating a tomographic image in the manner of a dental X-ray panoramic tomographic image from a digital 3D volume exhibiting X-ray absorption values, comprising transradiating the 3D volume virtually forming an object to be scanned using a virtual X-ray source, recording the virtually produced image by a virtual detector, and moving said virtual source of X-rays and said virtual detector virtually past the object to be scanned with formation of a sharp layer having a blurred area.

2. The method as defined in claim 1, further comprising removing, structures undesirable for, imaging from the 3D volume prior to creation of said tomographic image.

3. The method as defined in claim 1 or 2, further comprising adjusting a position of said sharp layer before or during creation of said tomographic image.

4. The method as defined in claim 3, further comprising modifying a distance of said sharp layer from said virtual X-ray source or from said virtual detector, in a direction normal to an X-ray source/detector plane of rotation.

5. The method as defined in claim 1 or 2, further comprising modifying at least one of a width of said virtual detector, a spread of a radiation fan beam, and a simulated speed of rotation of said virtual X-ray source and of said virtual detector, in order to control a thickness of the sharp layer.

6. The method as defined in claim 1 or 2, wherein said tomographic image is a panoramic tomographic image.

7. The method as defined in claim 6, wherein at least one of a distance of said X-ray source and of said detector from said sharp layer, a width of said detector, and blurred area, corresponds to a standard panoramic tomographic image.

8. The method as defined in claim 7, further comprising automatically determining a position of said sharp layer in the object from said 3D volume using a search algorithm for finding characteristic anatomical structures prior to creating said tomographic image.

9. The method as defined in claim 6, further comprising automatically determining a position of said sharp layer in the object from said 3D volume using a search algorithm for finding characteristic anatomical structures prior to creating said tomographic image.

10. The method as defined in claim 1 or 2, wherein said tomographic image is an image of a single tooth.

11. The method as defined in claim 10, further comprising automatically determining a position of said sharp layer in the object from said 3D volume using a search algorithm for finding characteristic anatomical structures prior to creating said tomographic image.

12. The method as defined in claim 1 or 2, further comprising automatically determining a position of said sharp layer in the object from said 3D volume using a search algorithm for finding characteristic anatomical structures prior to creating said tomographic image.

* * * * *

UNITED STATES PATENT AND TRADEMARK OFFICE
CERTIFICATE OF CORRECTION

PATENT NO. : 8,320,522 B2  
APPLICATION NO. : 12/855085  
DATED : November 27, 2012  
INVENTOR(S) : Johannes Ulrici et al.

Page 1 of 1

It is certified that error appears in the above-identified patent and that said Letters Patent is hereby corrected as shown below:

ON THE TITLE PAGE AT ITEM (63) RELATED U.S. APPLICATION DATA:

Insert --April 15, 2008  (US) ........... 61/071143--.

Signed and Sealed this  
Twenty-fourth Day of September, 2013

Teresa Stanek Rea  
*Deputy Director of the United States Patent and Trademark Office*